United States Patent [19]
James

[11] Patent Number: 5,026,993
[45] Date of Patent: Jun. 25, 1991

[54] APPARATUS FOR MONITORING SETTLEMENT OF A SOLID IN A LIQUID, AND A SYSTEM INCORPORATING SAME

[75] Inventor: David F. James, Hornchurch, England

[73] Assignee: Thames Water Utilities Limited, Reading, United Kingdom

[21] Appl. No.: 428,520

[22] Filed: Oct. 30, 1989

[51] Int. Cl.⁵ ............................................ G01N 21/01
[52] U.S. Cl. ................................ 250/357.1; 250/343; 250/573; 356/442
[58] Field of Search ..................... 250/357.1, 341, 343, 250/573; 356/442, 436

[56] References Cited

U.S. PATENT DOCUMENTS

| | | | |
|---|---|---|---|
| 3,319,514 | 5/1967 | McAllister | 356/442 |
| 3,441,737 | 4/1969 | Topol | 250/564 |
| 3,551,670 | 12/1970 | Topol | 250/357.1 |
| 3,586,862 | 6/1971 | Topol | 358/442 |
| 4,045,671 | 8/1972 | Dille et al. | 250/341 |
| 4,194,391 | 3/1980 | Rosenberger | 73/61.4 |
| 4,673,811 | 6/1987 | Rose | 250/573 |
| 4,719,359 | 1/1988 | Rose | 250/573 |
| 4,762,420 | 8/1988 | Bowley | 356/486 |

FOREIGN PATENT DOCUMENTS

| | | |
|---|---|---|
| 1549072 | 2/1979 | United Kingdom . |
| 1561667 | 2/1980 | United Kingdom . |
| 2174705A | 5/1985 | United Kingdom . |
| 2176290A | 12/1986 | United Kingdom . |
| 2187280A | 9/1987 | United Kingdom . |

*Primary Examiner*—Carolyn E. Fields
*Assistant Examiner*—Drew A. Dunn
*Attorney, Agent, or Firm*—Shapiro and Shapiro

[57] ABSTRACT

The invention relates to an automatic apparatus, computer controlled, for monitoring the settlement of solids in a liquid, specifically sludge in effluent from a sewage treatment plant. The apparatus enables the determination of the parameter known as the Stirred Specific Volume Index (SSVI) of the sludge. The apparatus includes a standard cylindrical vessel for receiving the sludge, and opposed banks of the LEDs and sensors which monitor the settlement height of the sludge as it settles in the liquid. Stirring is effected by an eccentric stirrer controlled by a Hall Effect device and the output from the sensors is fed to an electronic circuit fed by a computer for providing a determination of SSVI and hence control of a sewage works.

11 Claims, 6 Drawing Sheets

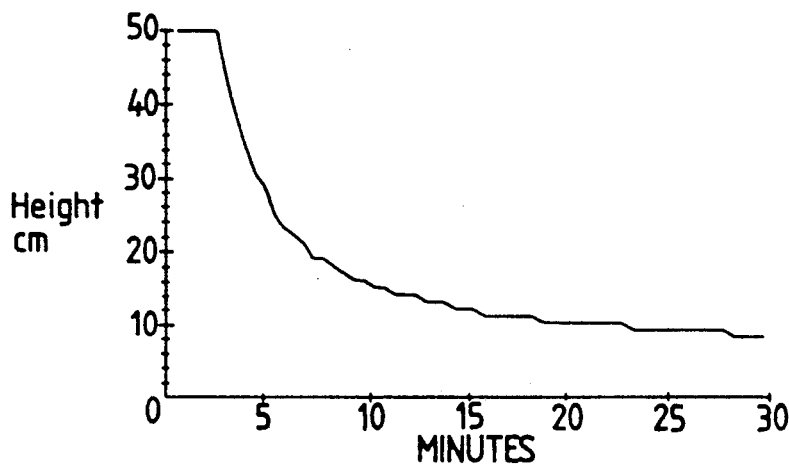

Report time : 3 17 50
Report date : 19 2 88
SUSPENDED SOLIDS for input stream 1 = 2876
SSV for input stream 1 = 55
RHS for input stream 1 = 4.800000001 m/h

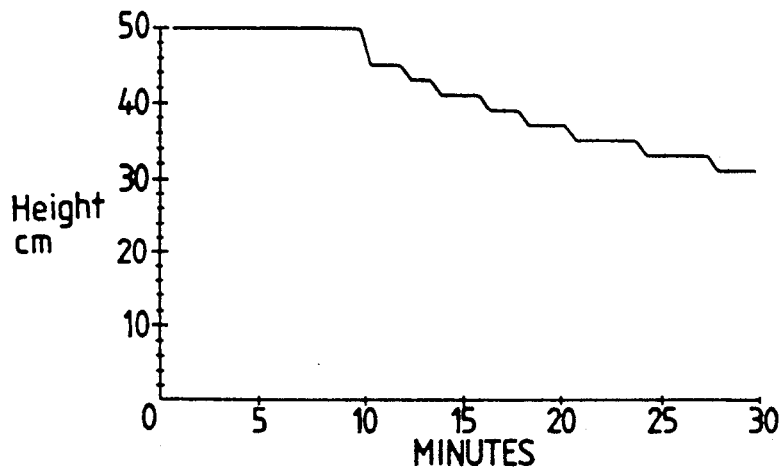

Report time : 3 53 4
Report date : 19 2 88
SUSPENDED SOLIDS for input stream 2 = 8368
SSV for input stream 2 = 74
RHS for input stream 2 = 0.6000000001 m/h
SETTLED SEWAGE FLOWRATE ENTERED AS 1500 litres/s
RECYCLE SLUDGE FLOWRATE ENTERED AS 450 litres/s

PARAMETERS DERIVED FROM SSV RESULTS :

INTERPOLATED SSV AT 3.5 g/litre = 57
UNDERFLOW RATE PER UNIT AREA OF FST = 0.6100000001 m/hour
TOTAL FLOWRATE PER UNIT AREA OF FST = 2.66 m/hour
APPLIED SOLIDS LOADING = 7 kg/m2/h
MAXIMUM SOLIDS LOADING = 9 kg/m2/h

FIG.8.

APPARATUS FOR MONITORING SETTLEMENT OF A SOLID IN A LIQUID, AND A SYSTEM INCORPORATING SAME

The invention relates to apparatus for monitoring settlement of a solid in a liquid, and a system incorporating same.

It is often necessary to monitor settlement rates of solids in liquids, for example in treatment of effluent such as sewage in an activated sludge process.

An apparatus is known for obtaining a parameter known as the Stirred Specific Volume Index (SSVI) of the sludge. The SSVI is a function of the settlement volume and the suspended solids concentration of the sludge and can produce useful control data for the process.

The parameter obtained from settlement of activated sludge over a 30 minute period using the apparatus is the Stirred Specific Volume (SSV). By interpolation, the SSVI at an intermediate solids concentration of 3.5 g/l may be obtained. A relationship between the SSVI at 3.5 g/l and final sedimentation tank (FST) performance have been established such that maximum FST solids loading and maximum FST underflow rates may be estimated from data which includes the SSVI.

Although the SSVI is determined routinely at many sewage works, the procedure is labour-intensive and in any case is impractical outside normal working hours or as a routine at an unmanned works.

It is accordingly an object of the invention to seek to mitigate these disadvantages.

According to the invention there is provided apparatus for monitoring settlement of a solid in a liquid, comprising a settlement vessel for containing the liquid, and automatic electronic means for sensing solids in the liquid.

It is to be understood that the term "settlement" used herein includes within its scope coagulation, flocculation and other processes whereby solids settle or become concentrated in liquids.

Using the invention it is possible to provide data about the settlement characteristics of activated sludge. Such data is useful for control purposes, since it may be used to predict safe flow and solids loadings to final sedimentation tanks (FST's).

The automatic sensing means may comprise a plurality of infra-red LEDs on one side of the vessel and a plurality of horizontally opposed infra-red sensors on an opposite side of the vessel.

There may be thirty pairs of LEDs and sensors each spaced vertically over the length of the vessel.

The pairs of LEDs and sensors may be arranged in two sets vertically, the spacing between adjacent LEDs and sensors in one, upper, set being different from that of the other, lower, set, as considered in use.

The spacing in the one set may be 2 cm, and in the other set may be 1 cm.

There may be electronic circuit means to actuate the automatic sensing means.

The apparatus may include a stirrer.

An electronic control circuit means for the stirrer may be adapted to cease rotation of the stirrer when the stirrer is at an angle to the optical path between the LEDs and sensors.

The electronic control circuit means for the stirrer may comprise Hall Effect means.

The Hall Effect means may comprise a fixed Hall Effect switch and a magnet mounted on the stirrer.

The switch may be mounted on a housing for a motor for rotating the stirrer.

The invention may extend to a system for monitoring settlement of activated sludge, incorporating apparatus as hereinbefore defined.

Apparatus and a system incorporating same, embodying the invention are hereinafter described, by way of example, with reference to the accompanying drawings.

FIG. 8 shows graphically results obtained using the apparatus of FIGS. 1-7.

Figures 1, 2:
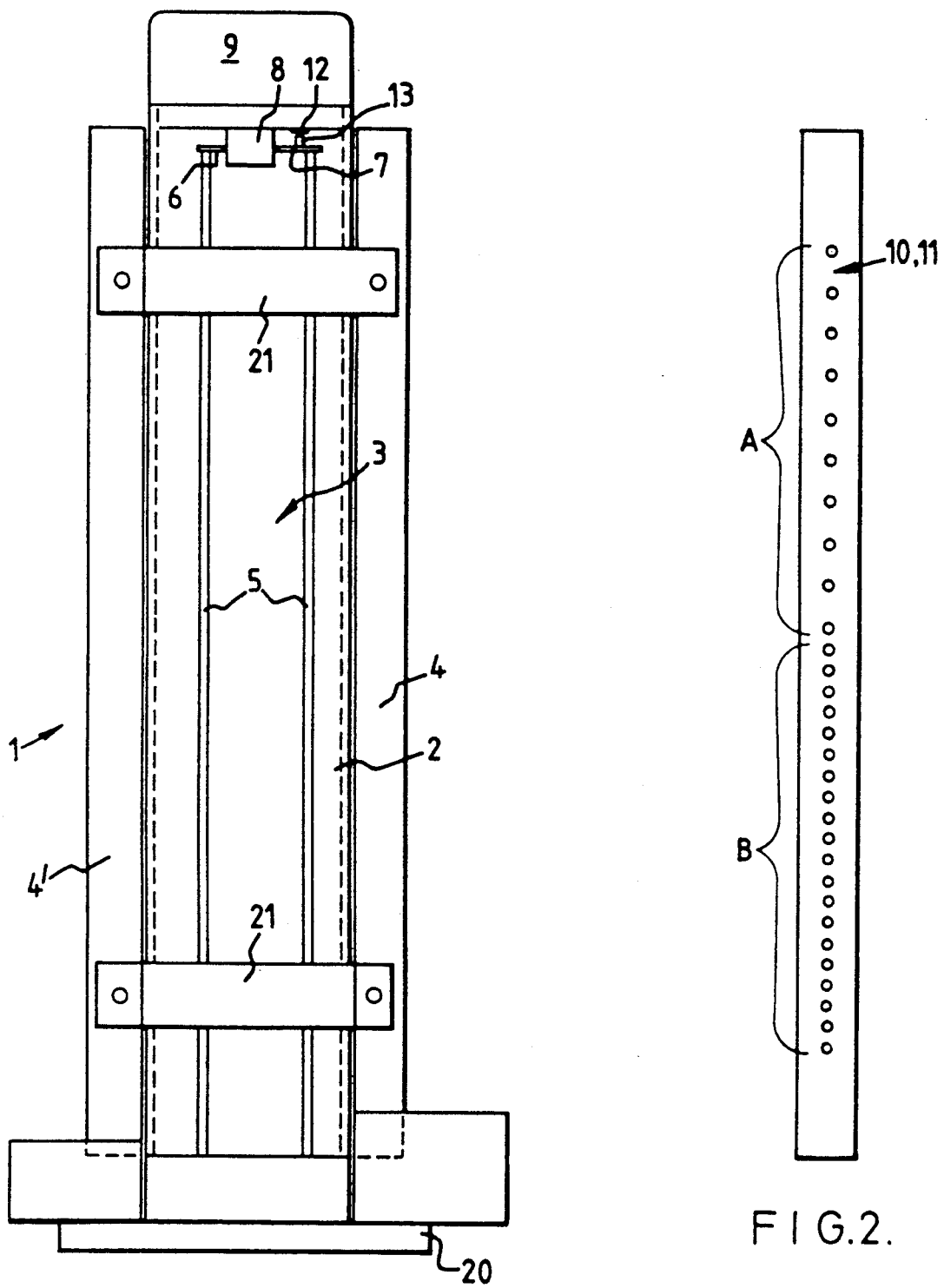
FIG. 1 is a schematic side elevational view of apparatus for monitoring settlement of a solid in a liquid, specifically sewage.
FIG. 2 is a schematic side elevational view of part of automatic sensing means of the apparatus of FIG. 1.

Referring to the drawings, there is shown apparatus 1 for monitoring settlement of a solid in a liquid, comprising a settlement vessel 2 for containing the liquid, specifically sewage containing solids in the illustrative embodiment, and automatic means 4, 4' for sensing solids' height in the liquid. The apparatus in this embodiment also includes a stirrer 3 adapted to provide uniform settlement in the vessel 2. The vessel 2 is substantially upright.

The vessel 2 is a transparent 100 cm diameter cylinder of nominal 50 cm settlement depth, and the stirrer 3 is an eccentric stirrer comprising two substantially parallel bars 5 each suspended from a respective arm 6 and 7 which arms in turn project from a drive spindle 8 of an electric motor which is in a housing 9 on top (as viewed) of the apparatus 1. The arm 7 is longer than the arm 6, to achieve the eccentric stirring effect to and uniform settlement of solids in the sewage. The vessel 2 has 20 mm i.d. inlet and outlet ports, a 20 mm overflow port and logic control of the eccentric stirrer.

The automatic sensing means 4,4' measures the depth of solids' settlement in the vessel 2 and comprises a plurality of infra-red LEDs (light emitting diodes) 10 arranged in a vertical array on one side of the vessel 2 and a plurality of infra-red sensors 11 arranged in a vertical array on the opposite side of the vessel 2, the LEDs 10 and sensors 11 being horizontally opposed in pairs. The LEDs 10 and sensors 11 are each arranged in two sets A and B vertically, adjacent LEDs/sensors of the, upper set A being spaced aparr vertically by 2 cm while the vertical spacing of adjacent LEDs/sensors in the lower set B is 1 cm. The closer spacing at B, near the bottom of the housing, is to provide a better response at lower settling rates in this region. There are ten LEDs/sensors in the, upper set A and twenty in the lower set B, making thirty in all. The sensors 10,11 determine the position of the sludge effluent interface.

Both the LEDs and photodiodes are fixed into sheet aluminum housings with epoxy resin, the aluminum shielding the photodiodes from stray and ambient infrared radiation.

Figure 4:
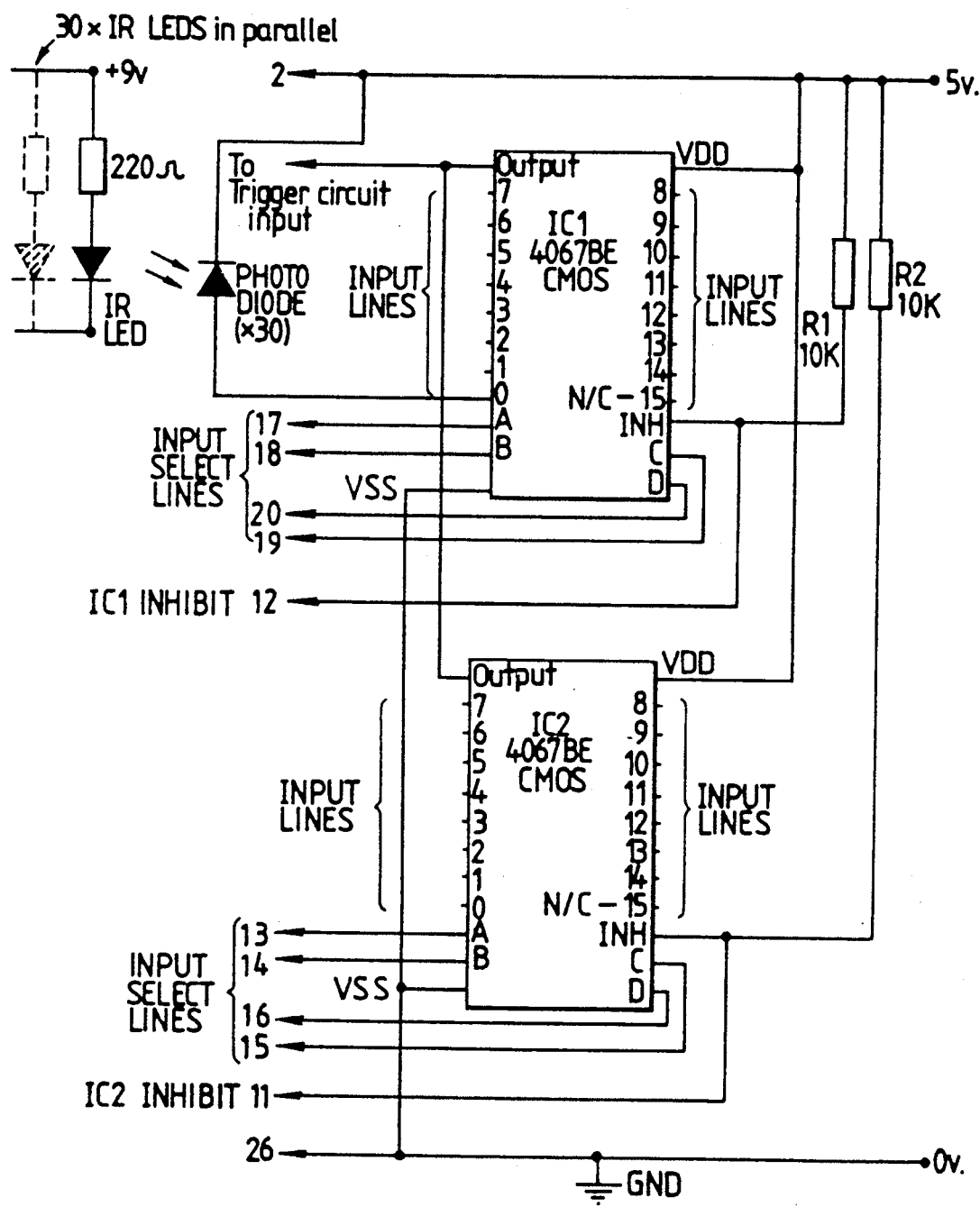
FIGS. 4-6 are circuit diagrams respectively for operation of the monitoring means trigger circuit and stirrer switch.
Figure 5:
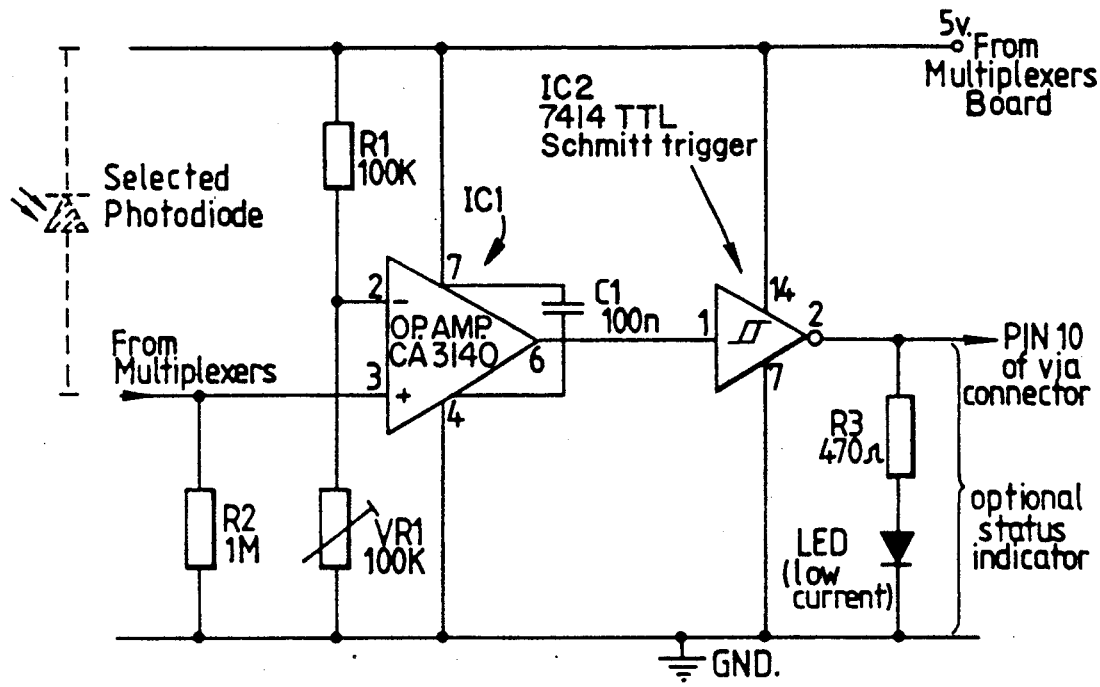

The sensing means 4,4' is controlled electronically and automatically by suitable circuitry, for example as shown in FIGS. 4 and 5 to be discussed later.

Figure 6:
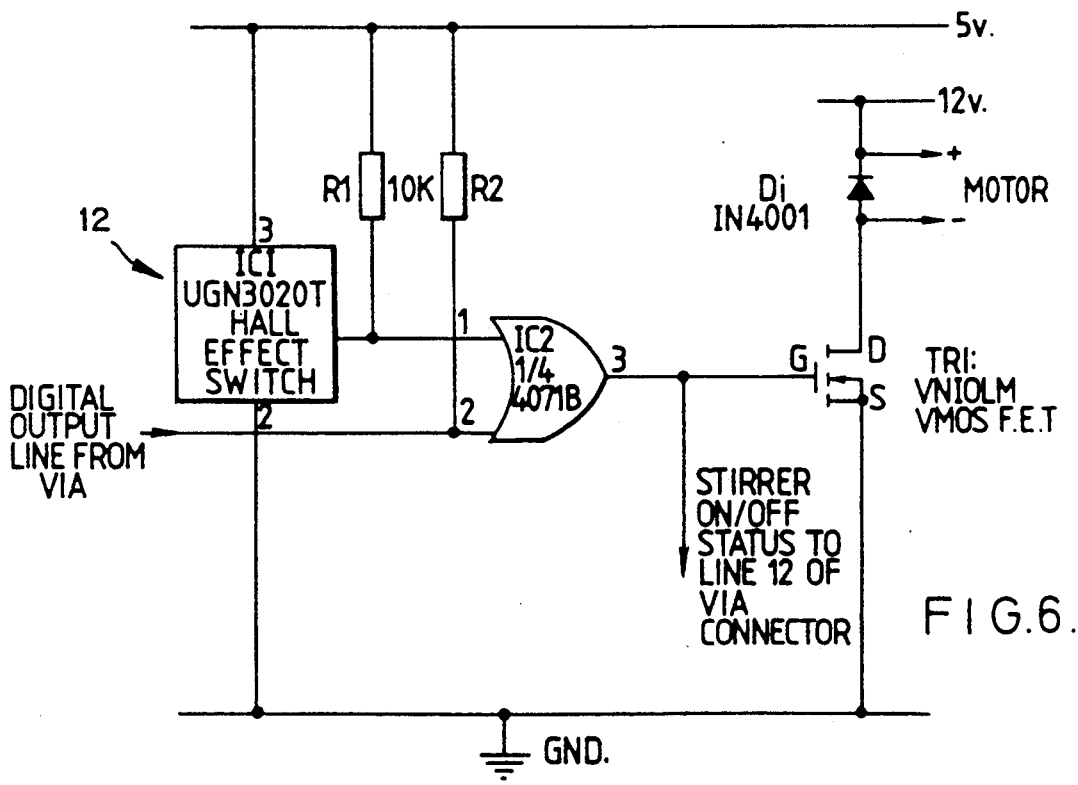

The eccentric stirrer 5 revolves at 1 rpm and in order to ensure an optical path between the sensors 11 and 10 and LEDs uninterrupted by anything other than sludge solids during measurement, electronic means (FIG. 6) is provided to switch the stirrer off when it is 90° away from the light beam, thus ensuring reliable readings. The electronic means includes a Hall Effect device in the form of a Hall Effect switch 12 mounted flush with the bottom (as viewed, FIG. 1) face of a housing 9 for the motor of the stirrer 5. A suitable magnet 13 is mounted on top of the longer arm 7 of the stirrer 5 so that it passes under the switch 12 with a vertical separation of about 2 mm every revolution of the stirrer. The action of the magnet 13 is to pull the switch 12 output low whilst in close proximity. Referring to FIG. 6, the output from IC1, which provides the Hall effect switch, is fed to an input of one of the gates of IC2, a CMOS 4071B Quad 2 input OR gate.

The other input to the gate is controlled by computer (not shown) by way of a digital output line from the computer interface board (not shown). Resistors R1 and R2 serve to pull the inputs high to provide a default condition.

In order to switch off the stirrer, input 2 of IC2 is taken low by the computer. The output of the gate will remain high, however, as input 1 is held high by the output from IC1. When the magnet reaches IC1 the output from IC1 goes low and thus the output from IC2 also goes low. This switches off the gate of TR1 which then prevents any current from reaching the stirrer motor.

Once the sensors have been read (in a manner to be discussed shortly), input 2 of IC2 is taken high under software control. This in turn takes the output of the OR gate high which excites the gate of TR1, switching it on and thereby IC2, input 2 of the OR gate may be taken low in anticipation of the next revolution of the stirrer when the process repeats itself.

Additionally, the output from the OR gate is monitored by the computer in order to check that the Hall Effect switch has in fact turned off and that readings may commence.

The circuit itself is mounted on a board inside the motor housing.

Figure 3:
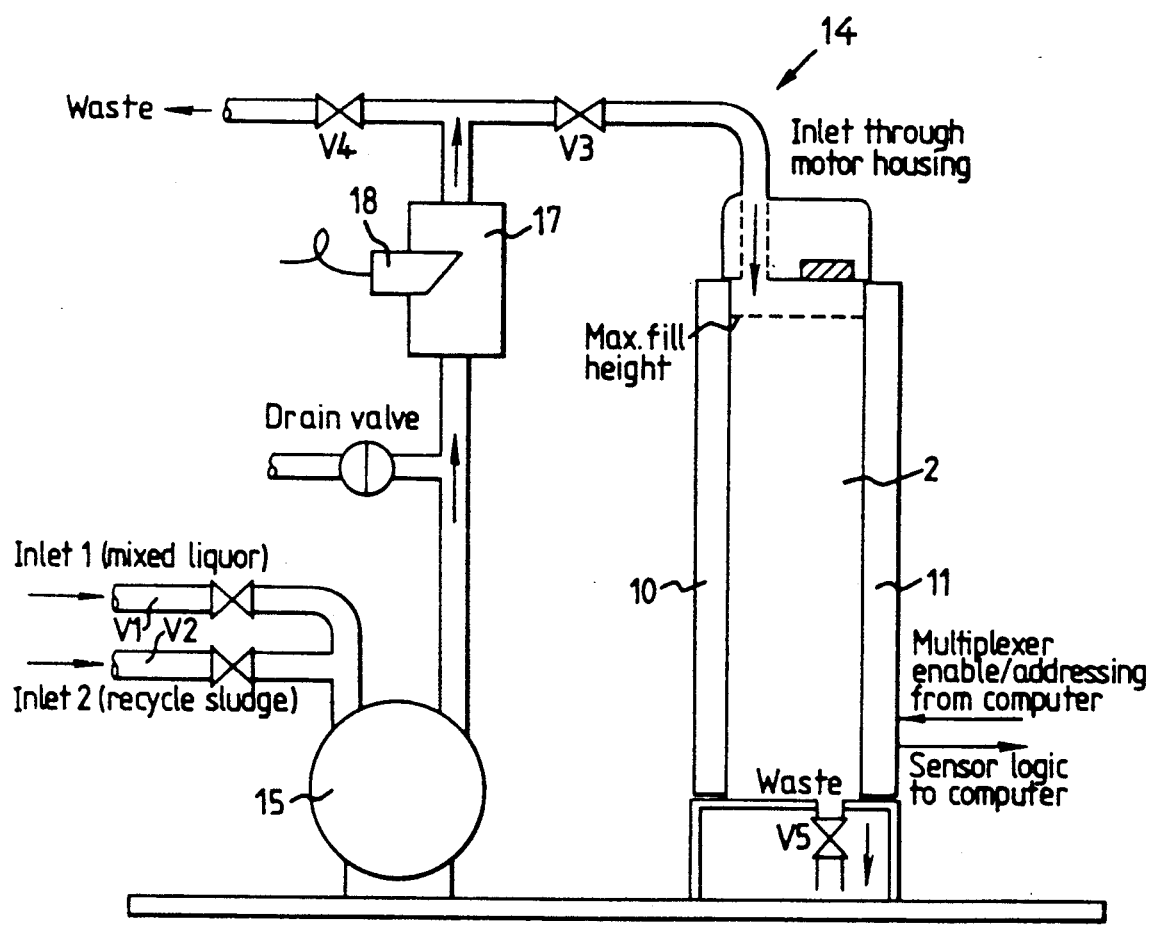
FIG. 3 is a schematic representation of a system incorporating apparatus as shown in FIGS. 1 and 2.

A system 14 for monitoring settlements of solids in sewage sludge to obtain a parameter for settlement of activated sludge over a 30 minute period, the Stirred Specific Volume (SSV), is shown in FIG. 3. The system includes the apparatus 1, and a pump 15, a 'Mono' type MS, which may be kept running continuously in a waste mode.

Flowstream switching is achieved via pneumatically actuated valves V1-V5, which are themselves controlled by pilot solenoid valves. These are in turn controlled by solid state relays connected to TTL logic outputs of the computer. The positive displacement pump 15, which is also controlled by the computer, provides a flowrate sufficient to fill the settlement cylinder in 10 to 15 seconds.

Suspended solids are measured using a pre-calibrated suspended solids monitor 18 built into a flow cell 17 above the pump output port. The output from the monitor 18 is fed to a 12 bit analog to digital converter (ADC) (not shown) to provide a resolution of 1 part in 4096.

A solid state level sensor in the wall of the settlement vessel or cylinder 10 is used to control switching of the valves when the cylinder is filled to the 50 cm mark. Additionally, a safety overflow is provided to prevent any overfill.

Actual settlement height of sludge is determined by scanning the array of infra-red photodiodes arranged vertically down the settlement cylinder. These are supplied with infra-red light by the complementary array of LEDs on the other side of the cylinder. The computer then utilizes a 'lookup' table to calculate the height of the sludge/effluent interface.

In addition to suspended solids and settlement data, details of settled sewage flowrate, recycle flowrate and total FST surface area are required in order to perform tank loading calculations. Linking of the system to flow metering equipment is feasible on works where such signals are readily accessible, thus presenting the possibility of on line measurement and control of FST loading.

Final data output is in the form of a settlement curve and a printed report (FIG. 8) from a small printer/plotter (not shown).

A total of five pneumatically actuated valves V1-V5 are used within the system 14, both for selection of input flowstream and also for re-direction of the selected flow. The valve actuators are supplied with compressed air at 8 bar via GEMU type 322 pilot solenoid valves. These pilot valves are actuated via solid state 240 v relays, which are themselves switched by TTL logic levels from a digital I/O port on the computer.

Compressed air for the valves is supplied by, for example, a JUN-AIR Minor compressor with pressure vessel.

The pump 15 is a Mono pump used to pump the sludge to the vessel 10. This pump is capable of filling the settlement cylinder 10 within 10 to 15 seconds and is self priming, provided the stator/rotor assembly has been wetted. (It will also run 'dry' for extended periods without damage, should the input flowstream be lost.)

The mixed liquor and recycle sludge suspended solids (MLSS and RSSS) are measured by the suspended solids monitor 18 mounted in the flowcell 17 above the pump 15 outlet. This provides linearity over the working range of 1000 to 8000 mg/liter solids, regression analysis being used accurately to determine the slope and intercept of the calibration line.

A solid state liquid level switch is used to detect the point at which the vessel 10 is full. The sensor output is connected to a digital input on the computer which generates a software interrupt when the vessel 10 is full. An overflow, accurately aligned at the 50 cm fill mark, ensures reproducible filling.

Infra-red light is supplied to the sensors 11 by the complementary array of LEDs 10. As shown in FIG. 4, these are supplied with power by a 9 v dc supply, the current being limited by a 220 Ω resistor between each anode and the supply. The cathodes are commoned, as are the cathodes of the photodiodes.

The photodiodes 11 are scanned in turn using the circuit shown in FIG. 4. The top 15 diodes have their anodes connected to input lines 0 to 14 of IC1, in the embodiment a CMOS 4067 16 way analog multiplexer (MUX). These connections are duplicated with the lower 15 diodes and IC2. All of the cathodes are commoned to a 5 v supply, derived from the computer I/O port. The 4067 MUX is a tri-state device, having an enable/inhibit input. If this line is taken low (0v), the chip is 'enabled', and by placing the appropriate binary code on the address lines A–D, the complementary input line will be connected to the output line. A truth table for the multiplexer is utilized. Only one of the MUX's is 'enabled' at any time, which means that the 5 outputs can be commoned together, effectively producing a 30-way MUX. Resistors R1 and R2 serve to pull the inhibit lines up to 5 v in order to provide a default condition where the chips are disabled.

Multiplexing in this way allows the anode of each photodiode in turn to be connected to the trigger circuit shown in FIG. 5. IC1 is a CA 3140 operational amplifier with its inputs across a bridge circuit The resistance of the selected photodiode and consequently the balance of the bridge itself may be offset via VR1. The circuit is balanced in this way whilst the photodiodes 11 are illuminated by the LEDs 10 with the vessel 2 filled with typical effluent Once this has been achieved, blocking of the light beam to the selected diode by sludge solids causes the bridge to go out of balance which then causes the output of IC1 to go fully positive. The output from IC1 is taken to IC2, in this case a 7414 TTL hex inverting Schmitt trigger. This ensures that the signal 'latches' cleanly at either logic state thus producing a TTL output suitable for connection to the computer I/O port By scanning the logic state of this signal after multiplexing each diode in turn, the position of the sludge/effluent interface may be calculated.

Figure 7:
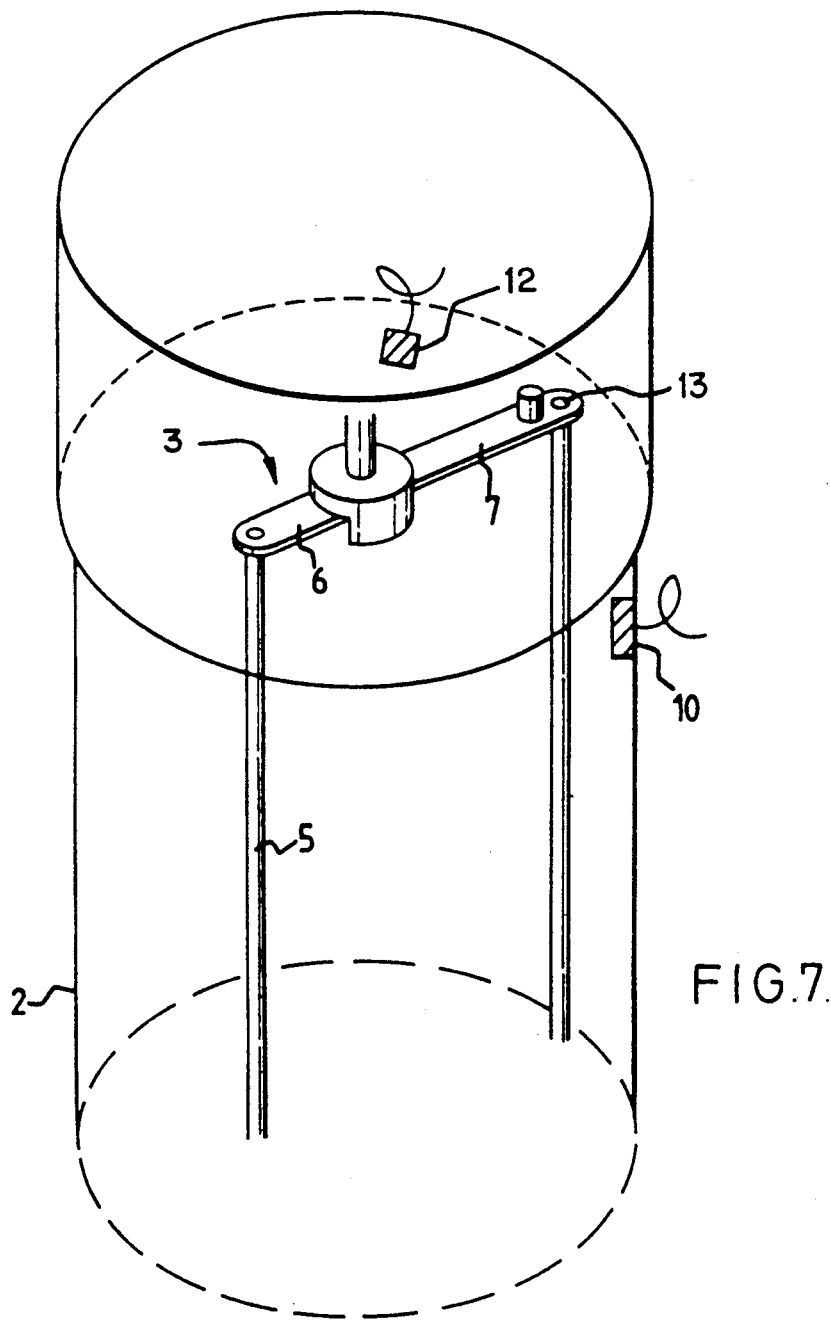
FIG. 7 shows an enlarged diagrammatic perspective view of the apparatus of FIG. 1, showing a Hall Effect switch detail.

As any optical method of settlement level measurement requires an uninterrupted beam (other than interruption by sludge solids), computer control of the stirrer and the ability to sense the stirrer position is incorporated. The circuit used is shown in FIG. 6, whilst the physical arrangement is shown in FIG. 7. A Hall Effect switch 12 is mounted flush with the bottom face of the motor housing A suitable magnet 13 is mounted vertically on top of the longer arm 7 of the stirrer 5 so that it passes under the switch 12, with a vertical separation of about 2 mm, once every revolution. The action of the magnet 13 is to pull the switch 12 output low whilst in close proximity. The output is fed to one of the pair of inputs to one of the gates of IC2, a CMOS 4071 quad 2-input OR gate. The other input to the gate is supplied by a digital output line from the computer I/O board. Resistors R1 and R2 serve to pull the inputs high to provide a default condition. In order to switch off the stirrer 5, input 2 of IC2 is taken low (Ov) by the computer. The output of the gate will remain high, however, as input 1 is held high by the output from IC1. When the magnet 13 reaches IC1 the output from IC1 goes low and thus the output from IC2 goes low also. This switches off the gate of TR1 which then prevents any current from reaching the stirrer motor. To switch the motor on again, all that is necessary is to take input 2 of IC2 high again under software control. This causes the output of IC2 to go high, which in turn excites the gate of TR1, which switches on to allow power to the stirrer motor. In addition, the output from IC2 is connected to one of the computer's digital inputs. This allows the status of the OR gate to be monitored, and to cause a software interrupt as soon as the magnet 13 reaches switch 12.

At the start of an operation of the system, once 20 mm id hose has been connected to all inlets, outlets and to the overflow, and the inlet or inlets have been immersed in a suitable source of sludge, power is applied to the system. The monitor screen displays a multi-choice set of options, for example:

(1) Run SSVI on Mixed Liquor only.
(2) Run Mixed Liquor & Recycle Alternately.
(3) Add or Amend Process Values.
(4) Reset System Clock.

Assuming that no process variables (settled sewage flow, recycle flow, number of FST's and surface area of an FST) have been entered, and that no options are selected from the keyboard within 30 seconds, program operation will continue automatically using option 1 as a default. The 30 second delay also allows the compressor's pressure vessel to fill in preparation. Option 3 allows values for the flowrates in litres/sec and FST data to be entered or edited, whilst option 4 allows review and reset of the real time clock. Both the process values and the clock are retained by battery backup. Once a valid run option has been selected, this will remain the default on subsequent program runs until changed.

Once a run option has been selected, the system checks the status of the level sensor and drains the vessel 10 if necessary (a power failure may have occurred when it was full). The settlement curve graph axes and titles are then displayed on the monitor. Valves V1 and V4 are then opened and the pump 15 is started. The software then arranges for the stirrer to be stopped under the Hall Effect switch 12 ready for the first scan of the photodiodes 11. A 3 minute flush cycle follows, at the end of which 50 samples are taken from the output of the solids monitor. The integerized mean of these samples represents the value of suspended solids in mg/litre. Valve V3 is then opened, whilst valve V4 is closed and the vessel 10 begins to fill. At this point, a software interrupt is enabled which automatically invokes a Multi-BASIC background 'task', the purpose of which is to stop the pump and close all valves as soon as the level sensor indicates that the vessel 10 is full.

The settlement routine then commences. The 30 sensors 11 are scanned via the 2 multiplexers, and the 'on' or 'off' status of each is stored in an array. Once a scan is complete, the array is checked to ensure that there is a complete series of 'on' sensors; i.e. sensors 11 which did not receive any light and are therefore below the level of the sludge/effluent interface. This enables the system to detect risen sludge and hence reject that particular run. If this is not the case, a 'lookup' table is consulted in order to correlate the position of the lowest 'off' sensor with the height of the interface. The stirrer 5 itself is only stopped momentarily in order to establish its position, and is immediately restarted. As the motor drives the stirrer 5 at 1 rpm, the scan is repeated 30 seconds later, when the stirrer is 180° away from its start position and then the Hall Effect switch 12 interrupt is enabled once more to await the return of the stirrer to its start position This process is repeated 30 times, to give 60 scans in the standard 30 minute settlement time. The sludge height after each scan is represented on the monitor as a vertical bar, so that as the settlement progresses, the rate of settlement is indicated by the reduction in height of the bars. The Rate of Hindered Settlement (RHS) is determined by counting the number of scans between the first sensor becoming exposed and the next sensor becoming exposed. As each scan takes place at 30 second intervals, a calculation of RHS in metres/hour is possible. In the event that the final settlement height is less than 8 cm, which is the height of the lowest sensor, the SSV is reported as being less than the SSV corresponding to a sludge whose final settlement height was actually 8 cm. At the end of the 30 minute settlement period, valve V5 is opened and the cylinder is allowed to drain for 20 seconds. A copy of the settlement curve is produced on the plotter, together with a printout of the results. The number of results calculated will vary, depending upon the run option selected or other factors. Once the mixed liquor results have been printed, the whole cycle is repeated. However, if alternate mixed liquor and recycle runs are being made, the sludge is pumped in via valve V2. In addition, under these conditions, data relating to FST loadings is calculated and reported at the end of the recycle settlement.

If mixed liquor alone is being examined, the suspended solids, SSVI and RHS are reported. If mixed liquor and recycle sludge are being settled alternately, the SSVI at 3.5 g/liter is interpolated, provided that the MLSS are less than 3.5 g/liter or that the RSSS are greater than 3.5 g/liter. If either of these conditions is met, a message is printed, stating that possible, the following results are output:

| | |
|---|---|
| (i) The sewage flowrate, as entered | leters/second |
| (ii) The recycle flowrate, as entered | leters/second |
| (iii) The interpolated SSVI at 3.5 grams/liter | mls/gram |
| (iv) The underflow rate per unit area of FST | meters/hour |
| (v) The total flowrate per unit area of FST | meters/hour |
| (vi) The applied solids loading | kg/m$^2$/hour |
| (vii) The calculated maximum solids loading | kg/m$^2$/hour |

In all cases, the settlement curve is also produced on tne plotter. An example of the settlement curves for mixed liquor and recycle sludge, together with the full report, is given in FIG. 8.

The apparatus 14 may be installed in a small towable trailer.

The detection of infra-red from the LEDs 10 is prone to interference from ambient IR. In a trailer of glass-reinforced plastic (GRP) construction, there is virtual transparency to the IR component of sunlight which can swamp the IR from the LEDs 10. The problem can be obviated by the addition of IR shield means, for example two half cylindrical PVC pipe sections, with aluminium foil bonded to them, which shield the vessel 10.

The pump 15 and valves are carried on an L-shaped bracket or carrier 16 of for example sheet plastic.

The LEDs 10, sensors 11 and associated circuitry are carried by a suitable frame or jig 20, for example of aluminium, which is complementary to and fits over the vessel, the sensors and LEDs being connected by straps 21 or the jig, and so that they are in use situated externally of the vessel 2.

In a modification, in order to seek to overcome interference of the IR light sensing at high levels of ambient IR:

(1) Instead of the present 2×4067 CMOS multiplexers, 4 may be used. The purpose is to allow both lines to each sensor 11 to be switched into the trigger circuit in isolation from the other sensors 11, thus preventing induced signals from any other sensors 11 from reaching the trigger circuit via the otherwise common cathodes.

(2) The IR LEDs 10 will be pulsed at a nominal 4 kHz, to provide a square wave output. An astable 555 timer chip, driving a 2N3055 power transistor is used to achieve this. The existing 12 v power supply is also used, although changing the square wave mark/space ratio (on/off period) would allow a smaller supply to be used.

(3) The trigger circuit may be modified to comprise a 486 IR pre-amp chip as its front end. Pulses detected by the sensor 11 under scrutiny may be amplified by this device to provide a signal level suitable for driving a 567 phase locked loop device. This chip is configured, by use by an external resistor and capacitor, to drive its internal oscillator at a 'free running' frequency of (in our case) 4 kHz. Circuits within the chip allow this frequency to be adjusted automatically when a pulse train sufficiently close to the free running frequency is detected at the input. When this occurs, the circuit is said to be 'locked' and will follow any small changes in frequency at the input. Under these conditions, a TTL compatible logic output is produced, which may be used to replace the logic output in the trigger circuit of the first embodiment. Using the apparatus described herein and shown in the drawings an automatic SSVI procedure under computer control is achieved, so that the SSVI is obtainable on an approximately hourly basis 24 hours a day, if necessary with minimal intervention other than routine cleaning and maintenance. The apparatus could also be used to measure the Rate of Hindered Settlement (RHS). RHS is produced by obtaining the slope of the straight portion of the curve produced by plotting height of settlement against time over the 30 minute period. RHS of the sludge at the mixed liquor concentration gives an indication of the maximum possible overflow rate for a final tank.

All calculations of SSVI are provided as follows:
Stirred Sludge Density:

$$SSD = \frac{\text{initial height} \times \text{initial concentration of } SS\ (\%)}{\text{height of interface after 30 minutes}}$$

Stirred Specific Volume Index:

$$SSVI = \frac{100}{SSD}$$

Underflow (recycle) rate per unit area of FST:

$$u = \frac{\text{Underflow rate m}^3/\text{h}}{\text{Total } FST \text{ area sq m}} \text{ m}^3/\text{m}^2 \text{ h}$$

Total flow rate per unit area of $FST =$ $$\frac{(\text{underflow} + \text{sewage}) \text{ m}^3/\text{h}}{\text{Total } FST \text{ area sq. m}}$$

Predicted maximum permissible solids loading on an FST:

$$F_L = 307\ (SSVI_{3.5})^{-0.77}\ (u)^{0.68} \text{ kg/m}^2 \text{ h}$$

where u is the rate of sludge recycle per unit area (m/h)
Applied solids loading = MLSS g/l × Tot. flowrate per unit area
N.B. the predicted solids loading is accurate to +/− 20%

I claim:
1. Apparatus for monitoring the rate of settlement of solids in a liquid, comprising:
    (a) a settlement vessel comprising means for containing said liquid;

(b) automatic electronic means for sensing the height of settled solids in the liquid in said vessel and comprising a plurality of infra-red LEDs at one side of said vessel, a plurality of infra-red sensors horizontally opposed to said LEDs at an opposite side of said vessel, and electronic circuit means for reading said sensors, with said LEDs and said sensors being arranged so as to define an upper set and a lower set of opposed LED-sensor pairs with a vertical spacing between successive LED-sensor pairs of the upper set being greater than that of the lower set;

(c) rotatable eccentric stirrer means disposed in said vessel for rotating between said LEDs and said sensors for effecting uniform settlement of the solids in the liquid in said vessel;

(d) electronic control circuit means for ceasing rotation of said stirrer means when said stirrer means is at an angle to an optical path between said LEDs and said sensors so as not to block said optical path; and (e) means shielding said vessel from ambient infra-red light.

2. Apparatus as defined in claim 1, wherien said spacing in said upper set is 2 cm, and in said lower set is 1 cm.

3. Apparatus as defined in claim 1, wherein said stirrer means comprises substantially horizontal upper and lower arms connected by substantially vertical stirrer elements.

4. Apparatus as defined in claim 3, wherein each of said arms comprises two arm parts one of which is longer than the other, said parts being connected at an axis of rotation of said stirrer means.

5. Apparatus as defined in claim 1, wherein said electronic control circuit means comprises Hall Effect means including a fixed Hall Effect switch and a cooperable magnet which is mounted on said stirrer means.

6. Apparatus as defined in claim 5, wherein said magnet is mounted on a longer upper arm part of said stirrer means, and wherein said switch is mounted on a housing for a motor for rotating said stirrer means.

7. Apparatus as defined in claim 1, comprising means for removing said shielding means.

8. Apparatus as defined in claim 7, wherein said shielding means comprises two aluminum shields which together shield said vessel.

9. Apparatus as defined in claim 8, wherein said vessel is cylindrical and wherein said shields are semi-cylindrical and respectively comprise aluminum sheet on a plastic body.

10. Apparatus as defined in claim 1, comprising means for mounting said settlement vessel in a vehicle.

11. A system for monitoring settlement of sludge in effluent from a sewage treatment plant, comprising:

(a) a settlement vessel comprising means for containing said effluent;

(b) automatic electronic means for sensing the height of settled sludge in the effluent in said vessel and comprising a plurality of infrared LED's at one side of said vessel, a plurality of infrared sensors horizontally opposed to said LEDs at an opposite side of said vessel, and electronic circuit means for reading said sensors, with said LEDs and said sensors being arranged so as to define an upper set and a lower set of opposed LED-sensor pairs with a vertical spacing between successive LED-sensor pairs of the upper set being greater than that of the lower set;

(c) rotatable eccentric stirrer means disposed in said vessel for rotating between said LEDs and said sensors for effecting uniform settlement of the sludge in the effluent in said vessel;

(d) electronic control circuit means for ceasing rotation of said stirrer means when said stirrer means is at an angle to an optical path between said LEDs and said sensors so as not to block said optical path; and (e) means shielding said vessel from ambient infrared light.

* * * * *